US006930077B2

(12) United States Patent
Glick et al.

(10) Patent No.: US 6,930,077 B2
(45) Date of Patent: Aug. 16, 2005

(54) COMPOSITIONS AND METHODS USING SUB-PPM COMBINATIONS OF POLYQUATERNIUM-1 AND HIGH MOLECULAR WEIGHT PHMB

(75) Inventors: Robert Glick, Lake Forest, CA (US); Stanley W. Huth, Newport Beach, CA (US); Zhi-Jian Yu, Irvine, CA (US); Charles H. Powell, Irvine, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 114 days.

(21) Appl. No.: 10/659,752

(22) Filed: Sep. 10, 2003

(65) Prior Publication Data

US 2005/0054546 A1 Mar. 10, 2005

(51) Int. Cl.[7] ........................ C11D 3/48; A61K 31/155; A61L 12/08

(52) U.S. Cl. ........................ 510/112; 510/382; 510/421; 510/473; 510/475; 510/504; 510/512; 514/839; 514/840; 424/78.04; 422/28

(58) Field of Search ................................ 510/112, 382, 510/421, 473, 475, 504, 512; 514/839, 840; 424/78.04; 422/28

(56) References Cited

U.S. PATENT DOCUMENTS 6,369,112 B1 * 4/2002 Xia ............................ 514/635

* cited by examiner

*Primary Examiner*—Brian P. Mruk
(74) *Attorney, Agent, or Firm*—Advanced Medical Optics, Inc.

(57) ABSTRACT

Multi-purpose solutions for contact lens care provide substantial lens wearer/user comfort and/or acceptability, with minimal, if any, corneal epithelial punctate fluorescein staining. Such solutions may include an aqueous liquid medium; an antimicrobial component comprising polyquarternium-1 and a hexamethylene biguanide polymer having a number average molecular weight in the range of from about 4,000 to about 45,000; a surfactant component, preferably a poly (oxyethylene)-poly(oxypropylene) block copolymer surfactant, in an effective amount; a buffer component in an effective amount; a viscosity-inducing component, preferably selected from cellulosic derivatives, in an effective amount; and a tonicity component in an effective amount. Such solutions have substantial performance, comfort and acceptability benefits, which, ultimately, lead to ocular health advantages and avoidance of problems caused by contact lens wear.

19 Claims, No Drawings

COMPOSITIONS AND METHODS USING SUB-PPM COMBINATIONS OF POLYQUATERNIUM-1 AND HIGH MOLECULAR WEIGHT PHMB

BACKGROUND OF THE INVENTION

1. Field of the Invention

The present invention relates to compositions and methods for contact lens care, and more particularly to contact lens disinfection using polyquaternium-1 and high molecular-weight poly(hexamethylene biguanide) antimicrobials for disinfection of contact lenses.

2. Description of Related Art

Contact lenses must be disinfected and cleaned to kill harmful microorganisms that may be present or grow on the lenses, and to remove any buildup that may have accumulated on the lenses. However, adverse changes in ocular tissues during contact lens wear may arise due to exposure of ocular tissues to preservatives, disinfecting agents, cleaning agents and other components in the contact lens care solutions. This can occur through tissue contact with solutions which may directly contact ocular tissues during application or tissue contact with solutions which may adsorb or absorb to the contact lens during treatment of the contact lens by the solution, and subsequently desorb into the eye from the contact lens during wear.

Generally, contact lenses in wide use fall into three categories: (1) hard lenses formed from materials prepared by polymerization of acrylic esters, such as polymethyl methacrylate (PMMA), (2) rigid gas permeable (RGP) lenses formed from silicone acrylates and fluorosilicone methacrylates, and (3) gel, hydrogel or soft type lenses. The hard and rigid-type lenses, because they are characterized by low vapor diffusion and absorb only minor amounts of aqueous fluids, have a lower tendency to bind ingredients used in contact-lens care solutions. On the other hand, soft lenses have a greater tendency to bind active ingredients in contact-lens solutions and, therefore, it is especially challenging to develop solutions designed for the treatment of soft-type lenses, whether made from the more traditional copolymers of 2-hydroxyethyl methacrylate (HEMA) or from the newer silicon-containing hydrogel materials. Silicon-containing hydrogel materials (silicone hydrogels), such as the Focus® NIGHT & DAY™ lens from CIBA Vision (Atlanta, Ga.) or the PUREVISION™ lens, comprised of the material balafilcon® A, from Bausch & Lomb, Incorporated (Rochester, N.Y.) are believed to have great potential in the contact lens market, due to their high rate of oxygen transmission and extended-wear capability.

After wear, contact lenses must be disinfected to kill harmful microorganisms that may be present or grow on the lenses. Some of the most popular products for disinfecting lenses are multi-purpose solutions that can be used to clean, disinfect and wet contact lenses, followed by direct insertion (placement on the eye) without rinsing. The ability to use a single solution for contact lens care is an advantage to many users. Such a solution must be strong enough to kill harmful microorganisms that may be present or grow on the lenses. It must also be particularly gentle to the eye, since at least some of the solution will be on the lens when inserted and will come into contact with the eye. Such a solution must also be compatible with all contact lens materials, particularly the silicone hydrogel materials, which represent the state-of-the-art contact lens materials. Contact lens compatibility is measured in several ways. Contact lens discoloration, physical parameter change, fragility and uptake and release of solution components, particularly antimicrobial agents, are all important. One important measure of clinical acceptance of the in-vitro uptake and release of antimicrobial agents is corneal epithelial punctate fluorescein staining. This measure of clinical acceptance is determined by instilling a small amount of a fluorescent dye, fluorescein, into the eye after removing a contact lens. Fluorescein binds only to damaged or dead corneal epithelial cells, which then can be detected with a suitable excitation light source to stimulate the fluorescence of the cell-bound fluorescein. Damaged or dead cells show up as bright fluorescent green points or bright or diffuse areas. Generally, a contact lens care solution, such as a multi-purpose solution (MPS), is considered to be compatible with a particular contact lens material, according to this measure of acceptance, when fluorescein staining is superficial, has a low ocular surface area and has a patient incidence of less than 10%.

U.S. Pat. No. 4,758,595 to Ogunbiyi et al. disclosed that a contact-lens solution containing a polyaminopropyl biguanide (PAPB), also known as poly(hexamethylene) biguanide (PHMB), has advantageous properties for a multi-purpose solution, especially in the presence of a borate buffer. These disinfecting and preservative solutions are especially noteworthy for their broad spectrum of bactericidal and fungicidal activity at low concentrations coupled with very low toxicity when used with soft-type contact lenses. Compositions containing PHMB and borate have been commercialized by Bausch & Lomb, Incorporated (Rochester, N.Y.) in various products including a multi-purpose solution, ReNu® MultiPlus®, at relatively low levels of about 1 ppm, for use with soft contact lenses. However, ReNu® MultiPlus® has been shown to produce an unacceptable incidence of 37% significant staining among PUREVISION™ (Bausch & Lomb Incorporated, Rochester, N.Y.) contact lens wearers by independent clinical investigators (Jones et al., *Asymptomatic Corneal Staining Associated with the Use of Balafilcon Silicone-Hydrogel Contact Lenses Disinfected with a Polyaminopropyl Biguanide-Preserved Care Regimen,* Optometry and Vision Science, Vol. 79, No. 12, December 2002).

Graham et al., in U.S. patent application Ser. No. 10/299,038 (Pub. No. US-2003-0129083-A1) disclose a multi-purpose solution comprising a poly(hexamethylene) biguanide (PHMB) disinfectant at 1 ppm in combination with the ophthalmic demulcents hydroxypropylmethylcellulose (HPMC) and propylene glycol, a poloxamer surfactant, a phosphate buffer and tonicity agent for disinfecting, cleaning and rewetting contact lenses. A composition of the invention has been marketed as Complete® Moisture Plus™ by Advanced Medical Optics, Incorporated (Santa Ana, Calif.). However, Complete® Moisture Plus™ has also been shown to produce a certain amount of staining among PUREVISION™ contact lens wearers by the same independent clinical investigators who evaluated ReNu®.

Asgharian, in U.S. Pat. No. 6,319,464, was able to achieve compatibility with silicone hydrogel contact lenses, Particularly PUREVISION® lenses from Bausch & Lomb, with a composition of the invention marketed as OPTI-FREE® EXPRESS® by Alcon, Incorporated in Fort Worth, Tex. A very low incidence of only 2% superficial fluorescein staining was observed (Jones et al., *Asymptomatic Corneal Staining Associated with the Use of Balafilcon Silicone-Hydrogel Contact Lenses Disinfected with a Polyaminopropyl Biguanide-Preserved Care Regimen,* Optometry and Vision Science, Vol. 79, No. 12, December 2002). However, this composition comprises five antimicrobial agents or adjuvants at concentrations well above 1 ppm each (Polyquaternium-1 (10 ppm), boric acid-sorbitol (600 ppm boric acid), disodium edetate (500 ppm), AMP-95 (4500 ppm) and myristamidopropyldimethylamine (MAPDA, at 5 ppm)). Together, these high concentrations of antimicrobial agents are very cytotoxic to mammalian cells (Mowrey-Mckee M, Sills A, Wright A. *Comparative cytotoxicity potential of soft contact lens care regimens,* The CLAO Journal 2002; 28 (3): 160–164). This level of cytotoxicity potentially can manifest itself in corneal tissue barrier function compromise and ocular discomfort, even in the absence of observable corneal epithelial punctate fluorescein staining.

A significant challenge to improving the disinfecting efficacy of a multi-purpose solution is to simultaneously improve or maintain its contact lens material compatibility and comfort. The addition of more effective disinfecting agents usually has the effect of reducing the material compatibility and comfort of the solution, in particular with silicone and non-silicone soft contact lenses and direct in-eye use. One way to achieve additional material compatibility and comfort is to lower the concentration of a disinfecting agent. However, this heretofore universally has resulted in lower antimicrobial efficacy. Also, it is known that polymeric biguanides, though chemically stable, can become partially depleted in solution over time due to sorption by the container walls, hence requiring a limited shelf life when used at relatively low concentrations that are preferred for comfort reasons.

Multi-purpose solutions that do not require digital rubbing of the contact lens with the solution as part of its regimen of use require more efficacious disinfection. Conventional contact-lens cleaners or disinfectants, including multi-purpose solutions, typically call for lens wearers to digitally or manually rub the contact lenses (typically between a finger and palm or between fingers) during treatment of the contact lenses. The necessity for the daily "rubbing" of contact lenses adds to the time and effort involved in the daily care of contact lenses. Many contact-lens wearers dislike having to perform such a regimen or consider it to be inconvenient. Additionally, some wearers are negligent in the proper "rubbing" regimen. This may result in contact-lens discomfort and other problems. Furthermore rubbing, if performed too rigorously, which is particularly apt to occur with beginning lens wearers, may damage the lenses. This can be especially problematic when a replacement lens is not immediately available.

Contact lens solutions that qualify as a "Chemical Disinfecting Solution" do not require rubbing to meet biocidal performance criteria (for destroying representative bacteria and fungi) set by the U.S. Food and Drug Administration (FDA) under the Premarket Notification (510 k) Guidance Document For Contact Lens Care Products, Appendix B, Apr. 1, 1997 and ISO/FDIS 14729: Ophthalmic optics—Contact lens care products—Microbiological requirements and test methods for products and regimens for hygienic management of contact lenses, January 2001. These aforementioned criteria are also known as the "stand-alone" disinfection standard. In contrast, a contact-lens solution, referred to as a "Chemical Disinfecting System," not qualifying as a Chemical Disinfecting Solution, requires a rubbing regimen to pass biocidal performance criteria. These criteria are known as the regimen standard.

FDA and ISO guidelines for disinfection efficacy standards follow:

Stand-Alone Disinfectant (Primary) Criteria:

| Organism | Average log reduction at labeled soak time |
|---|---|
| *S. marcescens,* ATCC 13880 | 3.0 logs |
| *S. aureus,* ATCC 6538 | 3.0 logs |
| *P. aeruginosa,* ATCC 9027 | 3.0 logs |
| *C. albicans,* ATCC 10231 | 1.0 log |
| *F. solani,* ATCC 36031 | 1.0 log |

Regimen-Dependent Disinfectant (Secondary) Criteria:

| Organism | Average log reduction at labeled soak time |
|---|---|
| *S. marcescens,* ATCC 13880 | Minimum of 1.0 log per bacterium, |
| *S. aureus,* ATCC 6538 | sum of all three bacteria log-drops |
| *P. aeruginosa,* ATCC 9027 | must be greater than or equal to 5.0 log |
| *C. albicans,* ATCC 10231 | Stasis |
| *F. solani,* ATCC 36031 | Stasis |

Traditionally, multi-purpose solutions (used for disinfecting and wetting or for disinfecting, cleaning, and wetting) have qualified as Chemical Disinfecting Systems, but not as Chemical Disinfecting Solutions. ReNu® MultiPlus® achieves the stand-alone disinfection standard, whereas Complete® Moisture Plus™ and other PHMB-containing multi-purpose solutions sold in the U.S. currently do not. OPTI-FREE® EXPRESS® also is marketed as a Chemical Disinfecting Solution, having passed the stand-alone standard.

Several investigators have explored the antimicrobial activity of different molecular weights of PHMB and other cationic polymers, in an attempt to optimize antimicrobial performance.

Broxton et al., in "Binding of some polyhexamethylene biguanides to the cell envelope of *Escherichia coli* ATCC 8739*", Microbios,* 41, 15–22, 1984, found that a 15 ppm solution of a high molecular weight fraction of PHMB with an n≧10 (corresponding to an unspecified molecular weight of ≧2436) showed greater than twice the antimicrobial activity against *Escherichia coli* ATCC 8739, as a 10 ppm solution of PHMB having a mean n=5.5 (corresponding to a molecular weight of 1446). In this study, however, *E. coli* cultures were prepared with centrifugation and washing. This same centrifugation and washing technique was proven in subsequent studies by the same research group to sensitize the cells towards higher molecular weights.

Gilbert et al., in "Barrier properties of the Gram-negative cell envelope towards high molecular weight polyhexamethylene biguanides", Journal of Applied Bacteriology, 69, 585–592, 1990, found that the antimicrobial activity of PHMB polymers against *E. coli* strains increased with polymer size within a series of polymers with polymerization numbers (n) of 4, 16, 30 and 35, corresponding to molecular weights of 1116, 3756, 6836 and 7936. More specifically, 1.8 ppm of the 7936 molecular weight material gave the same 1.0 log reduction in 1 minute against *E. coli* ATCC 8739 as 10.0 ppm of the 1116 molecular weight material, a 5.6-fold improvement. However, the same authors later reported that these results were obtained because the method of preparation of the cell suspensions employing both centrifugation and washing, leading to osmotic shock and losses of envelope lipopolysaccharide (LPS), sensitized the cells towards higher molecular weights (Gilbert et al., *Synergism within polyhexamethylene bigu-*

*anide biocide formulations,* Journal of Applied Bacteriology, 69, 593–598, 1990). The latter study reported that the lower molecular weight fractions (e.g., n=4) of PHMB were the most active against uncentrifuged, non-osmotically stressed cell suspensions of *E. coli* at in-use concentrations of 2.0 ppm or greater. Thus, attempts to optimize the antimicrobial activity of PHMB have failed.

Ikeda et al., in *Polycationic Biocides with Pendant Active Groups: Molecular Weight Dependence of Antibacterial Activity* (Antimicrobial Agents and Chemotherapy, July, Vol. 30, No. 1, 132–136, 1986), studied two cationic antimicrobial polymers: polymethylmethacrylate containing pendant biguanide units and poly(vinylbenzyl ammonium chloride). They found that antibacterial activity of the biguanide-containing polymer against *S. aureus* was optimal at an intermediate molecular weight range, about 5×10e4 to 10×10e4 g/mole, with lower and higher molecular weight polymers exhibiting lower activity. However, the activity of an antimicrobial agent against one organism such as *S. aureus* cannot be used to predict activity against other organisms. Furthermore, cationic polymer stability in aqueous solution is not a predictable phenomemon, especially with changing molecular weight.

Kirschner, et al., in U.S. Pat. No. 5,942,218, disclose an intravenously administratable anti-infection solution comprising PHMB wherein the weight proportion of the polymer containing 5 or less units per chain is less than 2% based on entire polymer weight. Particularly preferred PHMB materials are disclosed with mean molecular weights in the region of 3,200 to 5,000. Antimicrobial activity against *S. aureus* and *P. aeruginosa* of 5 ppm solutions of PHMB of mean molecular weights 3500 and 2610 are disclosed, wherein the higher molecular weight PHMB had higher activity. Surprisingly, 2.5× lower hemolytic activity against erythrocytes was also found with one of the higher molecular weight PHMB polymers. Use of these high molecular weight PHMB polymers with contact lenses was disclosed. However, no antimicrobial activity data with high molecular weight PHMB solutions containing concentrations suitable for contact lens use at concentrations about 1 ppm were presented. In fact, this reference teaches that suitable concentrations of PHMB lie in the range of between 0.001 through 0.05 wet. % (10–500 ppm), a concentration far beyond the acceptable range for contact lens applications. The reference also does not present any data on toxicity or cytotoxicity (which is very important when placing a solution in the eye) or on any specific American Type Culture Collection (ATCC)—designated microorganisms from the FDA contact lens disinfection panel. It is well known that different ATCC sub-species of the same organism can exhibit enormous differences in antimicrobial resistance. An example of this is the well known differences in the resistances of *Serratia Marcescens,* ATCC numbers 14041 and 16880. ATCC 14041 is very resistant to PHMB and other antimicrobials, whereas ATCC 19880 is much less so. ATCC 14041 was formerly on the FDA Soft Contact Lens Disinfection Panel of microorganisms, against which all manufacturers of disinfecting/multi-purpose solutions had to demonstrate activity. The 14041 organism was so resistant, however, that the contact lens solution manufacturers successfully lobbied the FDA to replace this organism with the less resistant 13880 organism, which is used today.

None of the aforementioned approaches to improving PHMB or other polymers has been successfully applied to either regimen or stand-alone contact lens disinfection, nor to achieving compatibility with silicone hydrogel contact lenses.

Thus, it would be desirable to obtain a multi-purpose contact-lens solution that would provide increased disinfecting and cleaning efficacy, particularly over time. Further, it would be desirable to increase the biocidal efficacy of the product without adversely affecting material compatibility, ocular comfort or safety in terms of the level of toxicity to eye tissue. Silicone hydrogel compatibility has therefore heretofore not been accomplished without utilizing high concentrations of antimicrobial agents and significantly contributing to solution cytotoxicity or in-eye discomfort. Thus, there is a need for a simple solution comprising a limited number of antimicrobial agents, at low concentrations, which can achieve silicone hydrogel compatibility without substantially increasing mammalian cell cytotoxicity and in-eye discomfort.

DETAILED DESCRIPTION

Compositions and methods using sub-ppm combinations of polyquaternium-1 and high molecular weight polyhexamethylene biguanide (PHMB) antimicrobials for disinfection of contact lenses have been discovered. The compositions and methods of the present invention provide for enhanced disinfection over multi-purpose contact lens solutions containing the equivalent amounts of either the PHMB or the polyquaternium-1, without significantly contributing to solution cytotoxicity, in-eye discomfort or corneal epithelial punctate fluorescein staining. The compositions and methods of the present invention achieve stand-alone disinfection standards against four of the five FDA contact lens disinfection panel organisms (*P. aeruginosa, S. aureus, S. marcescens* and *F. solani*) and regimen disinfection against the fifth organism, *C. albicans,* at less than 1 ppm polyquaternium-1 and less than 0.5 ppm PHMB concentration, using high molecular weight PHMB. This level of antimicrobial activity is considered to be superior to that of a current leading commercial contact lens multi-purpose solution, Optifree® Express® (Alcon Laboratories, Inc., Fort Worth, Tex., USA), in that the latter solution does not reliably meet the stand-alone disinfection standard against *S. aureus,* which is considered to be more important to kill than *C. albicans.*

Polyquaternium-1 is α-4-[1-tris(2-hydroxyethyl) ammonium-2-butenyl]poly[1-dimethylammonium-2-butenyl]-ω-tris (2-hydroxyethyl) ammonium chloride (available under the trademark Onamer M® from Onyx Chemical Company, Jersey City, N.J.; also known as Polyquad®, a registered trademark of Alcon Laboratories, Inc., Ft. Worth, Tex.; also known as polyquaternium-1). Its has been found that the combination of polyquaternium-1 and PHMB having number average molecular weight, $M_N$, in a range from about 4,000 to about 45,000, provides enhanced antimicrobial activity. As used herein, the term "high molecular weight PHMB" shall refer to PHMB having a molecular weight between from about 4,000 to about 45,000. PHMB having number average molecular weight, $M_N$, in a range from about 4,000 to about 14,000 provides even more enhanced antimicrobial activity, with PHMB having a number average molecular weight, $M_N$, in a range from about 4,000 to about 9,000 being the most beneficial for the present invention. In an alternate embodiment of the invention, PHMB having a number average molecular weight, $M_N$, in a range of greater than 5,000 to about 9,000 is used. These ranges pertain to methods of measuring PHMB number average molecular weight wherein the commercially available PHMB raw material Cosmocil® CQ (Avecia Limited, Manchester, U.K.) has a number average molecular weight of 3310.

In solution, the concentration of PHMB according to the present invention may be as low as from about 0.000005 to about 0.00009 w/v % (0.05 to 0.9 ppm). Preferably, the concentration is from about: 0.000005 to about 0.00005 w/v % (0.05 to 0.5 ppm), and even more preferably the concentration is from about 0.000005 to 0.000025 w/v % (0.05 to 0.25 ppm). In solution, the concentration of polyquaternium-1 according to the present invention may be as low as from about 0.000005 to about 0.00009 w/v % (0.05 to 0.9 ppm). Preferably, the concentration is from about: 0.00003 to about 0.00008 w/v % (0.3 to 0.8 ppm), and even more preferably the concentration is from about 0.00006 to 0.000075 w/v % (0.6 to 0.75 ppm). It will be understood by one of ordinary skill in the art that, while the present application only discusses polyquaternium-1 in conjunction with PHMB, other polyquaternium and biguanide polymers in combination at sub-ppm concentrations may also provide the same effect.

The polyquaternium-1 that may be used in the present invention may come in the form of a pure liquid, a liquid concentrate, a salt, or a salt in aqueous solution. One particularly useful form of polyquaternium-1 is polyquaternium-1 chloride in aqueous solution. Likewise, the PHMB that may be used in the present invention may come in the form of a pure liquid, a liquid concentrate, a salt, or a salt in aqueous solution. One particularly useful form of PHMB is a hydrochloride salt in aqueous solution at between 1 and 20 w/w %.

Molecular weight fractions of PHMB may be prepared in accord with any means known in the art including, but not limited to, molecular filtration, gel permeation chromatography (GPC), dialysis and chemical synthesis. Molecular filtration of various molecular weight fractions may be accomplished using molecular weight cut-off cellulose ester flat-sheet membranes (Molecular/Por® brand) (Spectrum Laboratories Inc., Rancho Dominguez, Calif.) and an associated fractionation apparatus. GPC separates molecules on the basis of molecular size, and the samples elute in decreasing order of molecular size. An example of an appropriate device to use for this procedure is the Waters Associate Model ALC/GPC 202 liquid chromatograph. GPC operates on the principle of molecular weight dependent retention time. The highest molecular weight polymer exhibits a decreased retention time because the individual molecules cannot enter the smaller pores of the stationary phase as in the case of the smaller size polymers. An example of an appropriate device to use for this procedure is the Waters 2690 Separation Module "Alliance", sold by Waters Corporation (Grand Rapids, Mich.). Dialysis uses the size difference between molecules to separate them using a semipermeable membrane, with the smaller molecules passing more efficiently through the dialysis membrane into an external solution. An example of an appropriate device to use for this procedure is the 96-Well Dialyzer™, sold by The Nest Group, Inc. (Southboro, Mass.). Chemical synthesis of polymeric biguanides is exemplified by the teachings of U.S. Pat. No. 5,741,886, which is incorporated herein in its entirety. Generally the hexamethylene biguanide polymers (PHMB), also referred to as poly(aminopropyl biguanide) (PAPB), have molecular weights of up to about 100,000. Such compounds are known and are disclosed in Ogunbiyi et al, U.S. Pat. No. 4,759,595, which is incorporated herein by reference.

In one embodiment, the present compositions comprise a liquid aqueous medium and a disinfecting component comprising a combination of polyquaternium-1 and high molecular weight PHMB in the liquid aqueous medium in an amount effective to disinfect a contact lens contacted with the composition. The PHMB component may have a number average molecular weight in a range of about 4,000 to about 45,000, wherein the PHMB component has been separated from a PHMB raw material having a number average molecular weight outside this range or the PHMB component has been chemically synthesized to result in this range. The solution further includes a surfactant component, preferably a nonionic surfactant, in an amount effective in cleaning a contact lens contacted with the composition; a buffer component in an amount effective in maintaining the pH of the composition within a physiologically acceptable range; an effective amount of a viscosity inducing component; and an effective amount of a tonicity component. The present compositions preferably include an effective amount of a chelating or sequestering component, more preferably in a range of less than 0.05% (w/v). Each of the components, in the concentration employed, included in the solutions and the formulated solutions of the present invention preferably are ophthalmically acceptable. In addition, each of the components, in the concentration employed, included in the present solutions is preferably soluble in the liquid aqueous medium.

A solution or component thereof is "ophthalmically acceptable" when it is compatible with ocular tissue, that is, it does not cause significant or undue detrimental effects when brought into contact with ocular tissue. Preferably, each component of the present compositions is also compatible with the other components of the present compositions. The present compositions are more preferably substantially ophthalmically optimized. An ophthalmically optimized composition is one which, within the constraints of component chemistry, minimizes ocular response, or conversely delivers ophthalmic benefit to the lens-wearing eye.

Additional antimicrobial components may be added to the present compositions. The presently useful additional antimicrobial components include chemicals which derive their antimicrobial activity through a chemical or physiochemical interaction with microbes or microorganisms, such as those contaminating a contact lens. Suitable antimicrobial components are those generally employed in ophthalmic applications and include, but are not limited to: quaternary ammonium salts used in ophthalmic applications such as benzalkonium halides, and biguanides, such as salts of alexidine, alexidine-free base, salts of chlorhexidine, hexamethylene biguanides, and salts thereof, antimicrobial polypeptides, and the like and mixtures thereof.

The antimicrobial components useful in the present invention preferably are present in the liquid aqueous medium in concentrations in the range of about 0.000005% to about 0.00009% (w/v). More preferably, the PHMB, polyquaternium-1, and any additional antimicrobial components are present in the liquid aqueous medium at an ophthalmically acceptable or safe concentration such that the user can remove the disinfected lens from the liquid aqueous medium and thereafter directly place the lens in the eye for safe and comfortable wear, with minimal, if any, incidence of corneal epithelial punctate fluorescein staining.

It has been found particularly advantageous to use a high molecular weight fraction of commercially available PHMB, or a chemically synthesized high molecular weight PHMB material in association with the present invention. High molecular weight PHMB provides increased activity with lower concentrations. This provides safe and comfortable wear, with minimal, if any, incidence of corneal epithelial punctate fluorescein staining.

When a contact lens is desired to be disinfected by the present compositions, an amount of the antimicrobial component effective to disinfect the lens is used. Preferably, such an effective amount of the antimicrobial component reduces the microbial burden or load on the contact lens by one log order in three hours. More preferably, an effective amount of the disinfectant reduces the microbial load by one log order in one hour.

The buffer component is present in an amount effective to maintain the pH of the composition or solution in the desired range, for example, in a physiologically acceptable range of about 4 or about 5 or about 6 to about 8 or about 9 or about 10. In particular, the solution preferably has a pH in the range of about 6 to about 8. The buffer component preferably includes one or more phosphate or tromethamine (TRIS, 2-amino-2-hydroxymethyl-1,3-propanediol) buffers, for example, combinations of monobasic phosphates, dibasic phosphates and the like, or tromethamine and tromethamine hydrochloride. Particularly useful phosphate buffers are those selected from phosphate salts of alkali and/or alkaline earth metals. Examples of suitable phosphate buffers include one or more of sodium phosphate dibasic ($Na_2HPO_4$), sodium phosphate monobasic ($NaH_2PO_4$) and the corresponding potassium phosphate salts. The buffer component may also include boric acid or sodium borate. The buffer component may also include an amino acid such as taurine. The present buffer components frequently are used in amounts in a range of about 0.01% or about 0.02% to about 0.5% (w/v), based upon buffer salt The present compositions preferably further comprise effective amounts of one or more additional components, such as a detergent or surfactant component; a viscosity inducing or thickening component; a chelating or sequestering component; a tonicity component; and the like and mixtures thereof. The additional component or components may be selected from materials which are known to be useful in contact lens care compositions and are included in amounts effective to provide the desired effect or benefit. When an additional component is included, it is preferably compatible under typical use and storage conditions with the other components of the composition. For instance, the aforesaid additional component or components preferably are substantially stable in the presence of the antimicrobial and buffer components described herein.

A surfactant component preferably is present in an amount effective in cleaning, that is to at least facilitate removing, and preferably effective to remove, debris or deposit material from, a contact lens contacted with the surfactant containing solution. Exemplary surfactant components include, but are not limited to, nonionic surfactants, for example, polysorbates (such as polysorbate 20-Trademark Tween 20), 4-(1,1,3,3-tetramethylbutyl) phenol/poly(oxyethylene) polymers (such as the polymer sold under the trademark Tyloxapol), poly(oxyethylene)-poly(oxypropylene) block copolymers, and the like, and mixtures thereof.

The surfactant component preferably is nonionic, and more preferably is selected from poly (oxyethylene)-poly (oxypxopylene) block copolymers and mixtures thereof. Such surfactant components can be obtained commercially from the BASF Corporation under the trademarks Pluronic® or Tetronic®. Pluronic® block copolymers can be generally described as polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol or glycerin. In the second step of the synthesis, ethylene oxide is added to sandwich this hydrophobe between hydrophile groups. Tetronic® surfactants are also known as poloxamines and are symmetrical block copolymers of ethylene diamine with polyoxyethylene and polyoxypropylene.

In accordance with a more preferred embodiment of the invention, such block copolymers having molecular weights in the range of about 2500 to 13,000 daltons are suitable, with a molecular weight range of about 6000 to about 12,000 daltons being still more preferred. Specific examples of surfactants which are satisfactory include: poloxamer 108, poloxamer 188, poloxamer 237, poloxamer 238, poloxamer 288 poloxamer 407, Tetronic® 1107, Tetronic®1304 (mwt 10,500), and Tetronic® 1307. Particularly good results are obtained with with poloxamer 237 and Tetronic® 1304. Poloxamer 237 is also known as Pluronic F87.

The amount of surfactant component, if any, present varies over a wide range depending on a number of factors, for example, the specific surfactant or surfactants being used, the other components in the composition and the like. Often, the amount of surfactant is in the range of about 0.005% or about 0.01% to about 0.1% or about 0.5% or about 1.0% (w/v). The preferred surfactant concentration is between about 0.05% and 0.20% (w/v).

The viscosity-inducing components employed in the present solutions preferably are effective at low or reduced concentrations, are compatible with the other components of the present solutions and are nonionic. Such viscosity inducing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the treated contact lens. The viscosity-inducing component may also act to cushion the impact on the eye surface during insertion and serves also to alleviate eye irritation.

Suitable viscosity-inducing components include, but are not limited to, water soluble natural gums, cellulose-derived polymers and the like. Useful natural gums include guar gum, gum tragacanth and the like. Useful cellulose-derived viscosity inducing components include cellulose-derived polymers, such as hydroxypropyl cellulose, hydroxypropylmethyl cellulose, methyl cellulose, hydroxyethyl cellulose and the like. More preferably, the viscosity-inducing agent is selected from cellulose derivatives (polymers) and mixtures thereof. A very useful viscosity inducing component is hydroxypropylmethyl cellulose (HPMC).

The viscosity-inducing component is used in an amount effective to increase the viscosity of the solution, preferably to a viscosity in the range of about 1.5 to about 30, or even as high as about 75 cps at 25° C., preferably as determined by USP test method No. 911 (USP 23, 1995). To achieve this range of viscosity increase, an amount of viscosity-inducing component of about 0.01% to about 5% (w/v) preferably is employed, with amounts of about 0.05% to about 0.5% being more preferred.

A chelating or sequestering component preferably is included in an amount effective to enhance the effectiveness of the antimicrobial component and/or to complex with metal ions to provide more effective cleaning of the contact lens.

A wide range of organic acids, amines or compounds which include an acid group and an amine function are capable of acing as chelating components in the present compositions. For example, nitrilotriacetic acid, diethylenetriaminepentacetic acid, hydroxyethylethylenediaminetriacetic acid, 1,2-diaminocyclohexane tetraacetic acid, hydroxyethylaminodiacetic acid, ethylenediaminetetraacetic acid and its salts, polyphosphates, citric acid and its salts, tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being particularly preferred.

The chelating component preferably is present in an effective amount, for example, in a range of about 0.01% and about 1% (w/v) of the solution.

In a very useful embodiment, particularly when the chelating component is EDTA, salts thereof and mixtures thereof, a reduced amount is employed, for example, in the range of less than about 0.05% (w/v) or even about 0.02% (w/v) or less. Such reduced amounts of chelating component have been found to be effective in the present compositions while, at the same time, providing for reduced discomfort and/or ocular irritation.

The liquid aqueous medium used is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 200-mOsmol/kg for example, about 300 or about 350 to about 400 mOsmol/kg. The liquid aqueous medium more preferably is substantially isotonic or hypotonic (for example, slightly hypotonic) and/or is ophthalmically acceptable.

The liquid aqueous medium preferably includes an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts and non-ionic polyols. Sodium chloride and/or potassium chloride and the like are very useful tonicity components, as are propylene glycol, glycerin, sorbitol, mannitol and the like. The amount of tonicity component included is effective to provide the desired degree of tonicity to the solution. Such amount may, for example, be in the range of about 0.4% to about 1.5% (w/v). If a combination of sodium chloride and potassium chloride is employed, it is preferred that the weight ratio of sodium chloride to potassium chloride be in the range of about 3 to about 6 or about 8.

Methods for treating a contact lens using the herein described compositions are included within the scope of the invention. Such methods comprise contacting a contact lens with such a composition at conditions effective to provide the desired treatment to the contact lens.

The contacting temperature is preferred to be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time in the range of about 5 minutes or about 1 hour to about 12 hours or more.

The contact lens can be contacted with the liquid aqueous medium by immersing the lens in the medium. During at least a portion of the contacting, the liquid medium containing the contact lens can be agitated, for example, by shaking the container containing the liquid aqueous medium and contact lens, to at least facilitate removal of deposit material from the lens. After such contacting step, the contact lens may be manually rubbed to remove further deposit material from the lens. The cleaning method can also include rinsing the lens with the liquid aqueous medium or substantially free of the liquid aqueous medium prior to returning the lens to a wearer's eye. However, the method may also be as simple as contacting a lens with a solution, and placing the lens directly in an eye.

The following non limiting examples illustrate certain aspects of the present invention.

EXAMPLE 1

Several contact lens multi-purpose solutions were formulated by dissolving the ingredients in Table 1 in deionized water. A high molecular weight PHMB of the present invention (10K PHMB) was employed, produced as a 10,000 molecular weight cut-off filter retentate from a molecular weight filtration of Cosmocil® CQ PHMB (Avecia Limited, Manchester, UK), resulting in a number average PHMB molecular weight of 4408. The number average molecular weight of Cosmocil® CQ is 3310. All formulas were sterile filtered using a sterile 0.22 micron cellulose acetate membrane. The resulting pH for all solutions was 7.8 and the solution osmolality was between 305–315 mOsm/kg. Antimicrobial activity was tested against the FDA contact lens disinfection panel. Log reductions at 6 hours solution contact are reported in Table 2. Two commercial contact lens multi-purpose solutions, Optifree® Express® and Complete® Moisture Plus™, were tested as controls.

As Table 2 shows, solutions 2, 3, 5 and 6 have the greatest activity. Surprisingly, solution 6 has comparable activity to solution 3, even though it has essentially the same amount of PHMB (0.20 vs 0.18 ppm) and only 0.44 ppm polyquaternium-1, versus the 0.97 ppm of polyquaternium-1 (PQ-1) in solution 3. Another surprising feature of the data is seen with the activity against *F. solani.* Solution 1, with 0.90 ppm PQ-1 and no PHMB, has an average log reduction of 2.3 for *F. solani* [(2.9+1.7)/2], whereas solution 2, with 0.90 ppm PQ-1 and 0.09 ppm PHMB, has an average log reduction of 1.51 for *F. solani.* Solution 3, with 0.97 ppm PQ-1 and 0.18 ppm PHMB, has an average log reduction of 1.70 for *F. solani.* Thus, the addition of a small amount of PHMB to PQ-1 reduces the antimicrobial activity of polyquaternium-1 against *F. solani.* A similar reduction in *F. solani* antimicrobial activity with the addition of PHMB to PQ-1 is seen with solution 6 (0.44 ppm PQ-1+0.20 ppm PHMB) versus solution 4 (0.44 ppm PQ-1) versus solution 8 (0.21 ppm PHMB). These results indicate a PHMB-antagonism of the activity of PQ-1 for *F. solani.* The antimicrobial activity of these solutions against *C. albicans* shows no such antagonism, however. A simple additive effect is seen in the *C. albicans* data. The activity of solution 6, with an average log reduction of 0.54, is essentially equal to the sum of the activities of solutions 4 (average 0.21 logs)+solution 8 (average 0.40 logs). Similarly, the 0.37 average log reduction for solution 2 is essentially equal to a simple sum of the average log reductions of solution 1 (0.26) and 7 (0.06). Note that in this and the other examples, the ingredient concentrations are expressed in w/w %, with the exception of the antimicrobial agents. However, given that multi-purpose solution density herein is essentially equal to 1.00 gm/mL, these w/w % concentrations are essentially equal to w/v % concentrations.

TABLE 1

| | Solution | | | | | | | |
|---|---|---|---|---|---|---|---|---|
| Ingredient | 1 | 2 | 3 | 4 | 5 | 6 | 7 | 8 |
| HPMC | 0.15 | 0.15 | 0.15 | 0.15 | 0.15 | 0.15 | 0.15 | 0.15 |
| Pluronic F87 | 0.05 | 0.05 | 0.05 | 0.05 | 0.05 | 0.05 | 0.05 | 0.05 |
| Na2EDTA | 0.01 | 0.01 | 0.01 | 0.01 | 0.01 | 0.01 | 0.01 | 0.01 |
| Propylene glycol | 0.5 | 0.5 | 0.5 | 0.5 | 0.5 | 0.5 | 0.5 | 0.5 |
| NaCl | 0.59 | 0.59 | 0.59 | 0.59 | 0.59 | 0.59 | 0.59 | 0.59 |
| KCl | 0.14 | 0.14 | 0.14 | 0.14 | 0.14 | 0.14 | 0.14 | 0.14 |
| Tris HCl | 0.055 | 0.055 | 0.055 | 0.055 | 0.055 | 0.055 | 0.055 | 0.055 |
| Tris base | 0.021 | 0.021 | 0.021 | 0.021 | 0.021 | 0.021 | 0.021 | 0.021 |
| Taurine | 0.05 | 0.05 | 0.05 | 0.05 | 0.05 | 0.05 | 0.05 | 0.05 |
| Polyquaternium-1, ppm | 0.90 | 0.90 | 0.97 | 0.44 | 0.49 | 0.44 | 0 | 0 |
| 10K PHMB, ppm | 0 | 0.09 | 0.18 | 0 | 0.12 | 0.20 | 0.12 | 0.21 |

Note:
All values are in w/w %, except PHMB and PQ-1

TABLE 2

| | Solution | | | | | | | | | |
|---|---|---|---|---|---|---|---|---|---|---|
| | 1 | 2 | 3 | 4 | 5 | 6 | 7 | 8 | Complete 9 | Optifree Express 10 |
| *S. aureus*, ATCC 6538 | 3.00 | >4.43 | >4.43 | 2.88 | >4.43 | >4.43 | 3.83 | 3.83 | >4.43 | 1.53 |
| *P. aeruginosa*, ATCC 9027 | >4.51 | >4.51 | >4.51 | 3.51 | 4.03 | >4.51 | 3.33 | 3.81 | >4.51 | >4.51 |
| *S. marcescens*, ATCC 13880 | 3.61 | >4.69 | >4.69 | 3.61 | >4.69 | >4.69 | 1.88 | 2.98 | >4.69 | 4.69 |
| *C. albicans*, ATCC 10231 | 0.35 | 0.30 | 0.51 | 0.24 | 0.36 | 0.48 | 0.00 | 0.30 | 1.12 | 3.80 |
| *F. solani*, ATCC 36031 | 2.90 | 2.80 | 2.9 | 2.30 | 1.40 | 1.40 | 0.00 | 0.70 | 1.70 | 3.00 |
| sum (all 5 organisms) | 9.86 | 16.73 | 17.04 | 12.54 | 14.91 | 15.51 | 9.04 | 11.62 | 16.45 | 17.53 |
| 2nd test: | | | | | | | | | | |
| *S. aureus*, ATCC 6538 | 2.86 | >4.64 | 4.64 | 2.57 | >4.64 | 4.16 | 3.44 | 2.96 | >4.64 | 2.81 |
| *P. aeruginosa*, ATCC 9027 | 4.65 | >4.65 | >4.65 | >4.65 | 4.65 | >4.65 | 3.8 | >4.65 | 4.65 | >4.65 |
| *S. marcescens*, ATCC 13880 | 2.27 | 4.12 | 4.72 | 2.19 | >4.72 | >4.72 | 1.69 | 2.26 | >4.72 | 3.31 |
| *C. albicans*, ATCC 10231 | 0.18 | 0.44 | 0.73 | 0.18 | 0.50 | 0.59 | 0.12 | 0.50 | 2.28 | >4.64 |
| *F. solani*, ATCC 36031 | 1.7 | 0.22 | 0.51 | 1.1 | 0 | 0.13 | 0 | 0 | 0.66 | 3.32 |
| sum (all 5 organisms) | 11.66 | 14.07 | 15.25 | 10.69 | 14.51 | 14.25 | 9.05 | 10.30 | 16.95 | 18.73 |
| average sum (all 5 organisms) | 10.76 | 15.40 | 16.15 | 11.62 | 14.71 | 14.88 | 9.05 | 10.96 | 16.70 | 18.13 |

EXAMPLE 2

Several contact lens multi-purpose solutions were formulated by dissolving the ingredients in Table 3 in deionized water. A high molecular weight PHMB of the present invention (10K PHMB) was employed as in Example 1, produced from a 10K molecular weight filter retentate of Cosmocil® CQ PHMB (Avecia Limited, Manchester, UK) molecular weight filtration, resulting in a number average PHMB molecular weight of 4408. The number average molecular weight of Cosmocil® CQ is 3310. None of the formulas were sterile filtered, to insure no filtration losses in antimicrobial agents. The resulting pH for all solutions was 7.8 and the solution osmolality was between 305–315 mOsm/kg. Antimicrobial activity was tested against the FDA contact lens disinfection panel. Log reductions at 6 hours solution contact are reported in Table 4. Two commercial contact lens multi-purpose solutions, Optifree® Express® and Complete® Moisture Plus™, were tested as controls. Solutions 714-92-3 and 714-92-4 have the greatest activity. Solution 714-92-3 has comparable activity to solution 714-92-4, while having a 20% reduction in concentration of both Polyquaternium-1 and PHMB. The antimicrobial activity against *F. solani* for the four solutions in this example is not inconsistent with the antimicrobial activity against *F. solani* of the solutions in example 1. A comparison of solution 714-92-4 and solution 3 illustrate this, the solutions having similar concentrations of PQ-1 and PHMB and similar activity.

TABLE 3

| | Solution | | | |
|---|---|---|---|---|
| Ingredient | 714-92-1 | 714-92-2 | 714-92-3 | 714-92-4 |
| HPMC | 0.15 | 0.15 | 0.15 | 0.15 |
| Pluronic F87 | 0.05 | 0.05 | 0.05 | 0.05 |
| Disodium Edetate | 0.01 | 0.01 | 0.01 | 0.01 |
| Propylene Glycol | 0.5 | 0.5 | 0.5 | 0.5 |
| NaCl | 0.59 | 0.59 | 0.59 | 0.59 |
| KCl | 0.14 | 0.14 | 0.14 | 0.14 |
| Tris HCl | 0.055 | 0.055 | 0.055 | 0.055 |
| Tris Base | 0.021 | 0.021 | 0.021 | 0.021 |
| Taurine | 0.05 | 0.05 | 0.05 | 0.05 |
| 10K PHMB | 0.08 ppm | 0.1 ppm | 0.16 ppm | 0.2 ppm |
| Polyquaternium-1 | 0.3 ppm | 0.38 ppm | 0.6 ppm | 0.75 ppm |

Note:
All values are in w/w %, except PHMB and Polyquaternium-1 Concentrations

TABLE 4

| microorganism | Test # | 714-92-1 | 714-92-2 | 714-92-3 | 714-92-4 | Optifree Express | Complete |
|---|---|---|---|---|---|---|---|
| *S. Marcescens* | 1 | 4.02 | 4.37 | >4.97 | >4.97 | 3.61 | >4.97 |
| ATCC 13880 | 2 | 2.68 | 3.72 | 2.93 | 3.82 | 3.61 | >4.72 |
| | 3 | 2.01 | 4.25 | >4.72 | >4.72 | 3.46 | >4.72 |
| | ave. | 2.90 | 4.11 | >4.20 | >4.50 | 3.56 | >4.80 |
| *S. Aureus* | 1 | 4.16 | >4.86 | >4.86 | 3.86 | 2.56 | >4.86 |
| ATCC 6538 | 2 | >4.69 | >4.69 | >4.69 | 4.32 | 3.24 | 4.34 |
| | 3 | 4.14 | >4.62 | >4.62 | >4.62 | 3.14 | >4.62 |
| | ave. | >4.33 | >4.72 | >4.72 | >4.27 | 2.98 | >4.61 |
| *P. Aeruginosa* | 1 | 4.74 | >4.74 | 3.74 | >4.74 | >4.74 | >4.74 |
| ATCC 9027 | 2 | 3.43 | >4.43 | >4.43 | 4.01 | >4.43 | >4.43 |
| | 3 | >4.61 | >4.61 | 3.53 | 3.91 | >4.61 | >4.61 |
| | ave. | >4.26 | >4.59 | >3.90 | >4.22 | >4.59 | >4.59 |
| *C. Albicans* | 1 | 0.28 | 0 | 0.09 | 0.39 | >3.54 | 1.16 |
| ATCC 10231 | 2 | 1.1 | 0.26 | 0.1 | 0.04 | >3.69 | 1.17 |
| | 3 | 0 | 0 | 0 | 0.31 | 4.45 | 0.99 |
| | ave. | 0.46 | 0.09 | 0.06 | 0.25 | >3.89 | 1.11 |
| *F. Solani* | 1 | 0.63 | 0.93 | 1 | 1.73 | 3.16 | 2.51 |
| ATCC 36031 | 2 | 0.8 | 1.39 | 1.84 | 1.81 | 3.81 | 2.44 |
| | 3 | 0.15 | 0.47 | 1.06 | 1.77 | >3.85 | 3.25 |
| | ave. | 0.53 | 0.93 | 1.3 | 1.77 | 3.61 | 2.73 |

Table 5 summarizes the stand-alone antimicrobial activity performance of the formulas in Tables 1 and 3 from Examples 1 and 2. FDA disinfection panel organism names are abbreviated as SM, SA, PA, FS and CA. A single stand-alone test failure for any organism reported in either Table 2 or 4 constitutes a test failure for that organism, except wherein the single test failure is within 0.10 log units of meeting the standard and wherein the overall test average for that particular organism exceeds the test standard. Optifree® Express® failed 3 out of 5 tests against *S. aureus,* whereas Complete® Moisture Plus™ failed 1 out of 5 tests against *F. solani,* according to the test failure criterion. Solutions 714-92-3 and 714-92-4 each failed 3 out of 3 tests against *C. albicans.* Other solutions failed more often against more organisms. A hierarchy of disinfection panel organism importance, in terms of which is most important to kill (disinfect), can be established, based upon: (1) the known incidence of ocular infections among contact lens wearers from a particular organism: gram-positive bacteria such a staphylococci and gram-negative bacteria such as *pseudomonas* and *serratia* species, cause most infections: Klotz S A et al. Contact lens wear enhances adherence of *Pseudomonas aeruginosa* and binding of lectins to the cornea. *Cornea.* 1990 July; 9(3):266–70; Willcox M D, et al. Bacterial interactions with contact lenses; effects of lens material, lens wear and microbial physiology. *Biomaterials.* 2001 December; 22(24):3235–47; Hume E B et al. Evasion of cellular ocular defenses by contact lens isolates of *Serratia marcescens. Eye Contact Lens.* 2003 Apr.; 29(2): 108–12; (2) inherent organism pathogenicity and virulence: strains of *pseudomonas* are particularly pathogenic and virulent in ocular infections, causing severe infection and permanent loss of vision in some cases: Vallas V et al. Bacterial invasion of corneal epithelial cells. *Aust N Z J Ophthalmol.* 1999 June–August; 27(3–4):228–30; *F. solani* has been shown to be more pathogenic and virulent in experimental infection of the rabbit cornea than *C. albicans:* Ishibashi Y, et al., Comparison of the pathogenicities of *Fusarium solani* and *Candida albicans* in the rabbit cornea. *J. Med Vet Mycol.* 1986 October; 24(5):369–76; (3) propensity to form resistant microbial biofilms (that predispose to infection) in contact lens cases and on contact lens surfaces: *staphylococci* and particularly *pseudomonas* strains form such biofilms: van Bijsterveld O P, et al., Infectious diseases of the conjunctiva and cornea. *Curr Opin Ophthalmol.* 1996 August; 7(4):65–70; (4) prevalence in environments such as bathrooms where contact lens cases are often kept and where lens care often takes place: bacteria and fungi such as *F. solani* predominate; and (5) antimicrobial activity of current ophthalmic antibiotics and their ability to successfully treat ocular infections: resistant strains of *S. aureus* currently pose a significant problem. Based upon these factors, the following hierarchy is established: (1) *P. aeruginosa,* (2) *S. aureus,* (3) *S. marcescens,* (4) *F. solani* and (5) *C. albicans,* with (1) being the most important to kill. Thus, solutions of the present invention, exemplified by 714-92-3 and 714-92-4, will have an inherent advantage over current commercial multi-purpose solutions, particularly over Optifree® Express®, in prevention of ocular infections and unsuccessful treatment outcomes. Moreover, given the low concentrations of the two antimicrobial agents employed in compositions of the present invention, little to no solution cytoxicity potential exists, unlike Optifree® Express®, which utilizes high concentrations of antimicrobial agents and exhibits high cytotoxicity. Also, given the low concentrations of the two antimicrobial agents employed in compositions of the present invention, contact lens material compatibility with all lens materials is achieved.

TABLE 5

| Solution | PHMB ppm | PQ-1 ppm | PA | SA | SM | FS | CA |
|---|---|---|---|---|---|---|---|
| | | | Stand-alone test failure | | | | |
| 1 | 0 | 0.9 | | X | X | | X |
| 2 | 0.09 | 0.9 | | | | X | X |
| 3 | 0.18 | 0.97 | | | | X | X |
| 4 | 0 | 0.44 | | X | X | | X |
| 5 | 0.12 | 0.49 | | | | X | X |
| 6 | 0.2 | 0.44 | | | | X | X |
| 7 | 0.12 | 0 | | | X | X | X |
| 8 | 0.21 | 0 | | | X | X | X |
| 714-92-1 | 0.08 | 0.3 | | | X | X | X |
| 714-92-2 | 0.1 | 0.38 | | | | X | X |
| 714-92-3 | 0.16 | 0.6 | | | | | X |
| 714-92-4 | 0.2 | 0.75 | | | | | X |
| Optifree | 0 | 10 | | X | | | |
| Complete | 1.1 | 0 | | | | X | |

EXAMPLE 3

A solution is prepared by blending together the components provided in Table 3, solution 714-92-4. Approximately three (3) mL of this solution is introduced into a lens case containing a lipid, oily and protein-deposit laden, hydrophilic or soft contact lens. The contact lens is maintained in this solution at room temperature for at least about four (4) hours. This treatment is effective to disinfect the contact lens. In addition, it is found that a substantial portion of the deposits previously present on the lens has been removed. This demonstrates that this solution has substantial passive contact lens cleaning ability. Passive cleaning refers to the cleaning which occurs during soaking of a contact lens, without mechanical or enzymatic enhancement.

After this time, the lens is removed from the solution and is placed in the lens wearer's eye for safe and comfortable wear. Alternately, after the lens is removed from the solution, it is rinsed with another quantity of this solution and the rinsed lens is then placed in the lens wearer's eye for safe and comfortable wear.

EXAMPLE 4

Example 3 is repeated except that the lens is rubbed and rinsed with a different quantity of the solution prior to being placed in the lens vial. This treatment is effective to disinfect the contact lens. In addition, it is found that a substantial portion of the deposits previously present on the lens has been removed. After at least about four (4) hours, the lens is removed from the solution. The lens is then placed in the lens wearer's eye for safe and comfortable wear.

EXAMPLE 5

The solution of Example 3 is used as a long-term soaking medium for a hydrophilic contact lens. Thus, approximately three (3) mL of this solution is placed in a vial and a contact lens is maintained in the solution at room temperature for about sixty (60) hours. After this soaking period, the lens is removed from the solution and placed in the lens wearer's eye for safe and comfortable wear. This treatment is effective to disinfect the contact lens. In addition, it is found that a substantial portion of the deposits previously present on the lens has been removed. Alternately, after the lens is removed from the solution, it is rinsed with another quantity of this solution and the rinsed lens is then placed in the lens wearer's eye for safe and comfortable wear.

EXAMPLE 6

A hydrophilic contact lens is ready for wear. In order to facilitate such wearing, one or two drops of the solution of Example 3 is placed on the lens immediately prior to placing the lens in the lens wearer's eye. The wearing of this lens is comfortable and safe.

EXAMPLE 7

A lens wearer wearing a contact lens applies one or two drops of the solution of Example 3 in the eye wearing the lens. This effects a re-wetting of the lens and provides for comfortable and safe lens wear.

EXAMPLE 8

Two contact lens multi-purpose solution formulas as indicated in Table 6 were prepared, each with identical components and concentrations except with respect to PHMB. Both solutions were tested against the FDA contact lens disinfection panel of microorganisms as in Example 1, with the exception that the solutions were not sterile-filtered prior to antimicrobial efficacy testing, to insure no losses of PHMB due to filter binding. Table 7 shows that both solutions meet the stand-alone disinfection efficacy standards, and that the solution containing 0.55 ppm (0.000055 w/v %) of a 10K retentate high molecular weight PHMB of the present invention has a significantly greater antimicrobial activity against *C. albicans* and *F. solani* than the solution containing 0.55 ppm of normal Cosmocil® CQ. An average 109% increase in activity against *C. albicans* and 57% increase in activity against *F. solani* were found for the solution containing the 10K retentate high molecular weight PHMB material of the present invention. Thus, this example, in combination with examples 1 and 2 and the analysis of stand-alone antimicrobial activity presented in Table 5, illustrates the advantage of using a high molecular weight PHMB in combination with Polyquaternium-1.

TABLE 6

Solution components for multi-purpose solution formulations (final concentrations shown).

| Ingredients | |
|---|---|
| Hydroxypropylmethyl Cellulose | 0.15% w/w |
| NaCl | 0.59% w/w |
| Propylene Glycol | 0.50% w/w |
| Potassium Chloride | 0.14% w/w |
| Tris hydrochloride | 0.055% w/w |
| Tris, base | 0.021% w/w |
| Taurine | 0.05% w/w |
| Edetate Disodium | 0.01% w/w |
| Pluronic F87 | 0.05% w/w |
| PHMB 10K retentate or Cosmocil ® CQ | 0.000055% w/v |

The pH of this solution was 7.8; the tonicity was 310 mOsm/kg.

TABLE 7

Antimicrobial activity at 6 hours contact.

| Organism | PHMB 10K retentate, Tests 1; 2 (Log) | Cosmocil ® CQ, Tests 1; 2 (Log) |
|---|---|---|
| *S. marcescens*, ATCC 13880 | >4.72; >4.15 | >4.72; >4.15 |
| *S. aureus*, ATCC 6538 | >4.62; >4.58 | >4.62; >4.58 |
| *P. aeruginosa*, ATCC 9027 | >4.61; >4.66 | >4.61; >4.66 |
| *C. albicans*, ATCC 10231 | 1.09; 1.90 | 0.38; 1.05 |
| *F. solani*, ATCC 36031 | 2.74; 2.28 | 1.77; 1.43 |

While this invention has been described with respect to various specific examples and embodiments, it is to be understood that the invention is not limited thereto and that it can be variously practiced within the scope of the following claims.

What is claimed is:

1. A multi-purpose solution for contact lens care comprising:

an aqueous liquid medium; and an antimicrobial component, the antimicrobial component comprising from about 0.000005 to about 0.00009 w/v % polyquaternium-1 and from about 0.000005 to about 0.00009 w/v % high molecular weight PHMB, wherein the PHMB has a number average molecular weight of from about 4000 to about 45,000, and further wherein the PHMB has been separated from PHMB material having a number average molecular weight outside said range or has been chemically synthesized to result in said range.

2. The solution as in claim 1, further comprising a surfactant in an amount effective to clean a contact lens contacted with said solution.

3. The multi-purpose solution of claim 2, wherein said surfactant is selected from the group consisting of poly(oxyethylene)-poly(oxypropylene) block copolymers and mixtures thereof, and is present in an amount in a range of about 0.01% to about 1.0% (w/v).

4. The solution as in claim 1, further comprising a buffer component in an amount effective in maintaining the pH of said solution within a physiologically acceptable range.

5. The multi-purpose solution of claim 1, further comprising a buffer component selected from the group consisting of tromethamine, tromethamine salts, phosphate salts, taurine and mixtures thereof in the range of about 0.01% to about 0.5% (w/v).

6. The solution as in claim 1, further comprising a viscosity-inducing component selected from the group consisting of cellulosic derivatives and mixtures thereof in the range of about 0.05% to about 5.0% (w/v) of the total solution.

7. The multi-purpose solution of claim 6 wherein said viscosity-inducing component is hydroxypropylmethyl cellulose.

8. The solution as in claim 1, further comprising a chelating component in an amount of less than 0.05% (w/v) of the total solution.

9. The multi-purpose solution of claim 8 wherein said chelating component is EDTA.

10. The solution as in claim 1, further comprising a tonicity component in an amount effective in providing the desired tonicity to said solution.

11. The multi-purpose solution of claim 10, wherein said tonicity component comprises a combination of sodium chloride and potassium chloride and is present in a range of about 0.4% to about 1.5% (w/v).

12. A method for disinfecting a contact lens comprising contacting the lens with an aqueous solution comprising from about 0.000005 to about 0.00009 w/v % polyquaternium-1 and from about 0.000005 to about 0.00009 w/v % high molecular weight PHMB, wherein the PHMB has a number average molecular weight of from about 4000 to about 45,000, and further wherein the PHMB has been separated from PHMB material having a number average molecular weight outside said range or has been chemically synthesized to result in said range.

13. The method for disinfecting as in claim 12, wherein the solution further comprises a component selected from the group consisting of a buffer, a surfactant, a viscosity inducing agent, a chelating agent and a tonicity component.

14. The method for disinfecting as in claim 13, wherein said surfactant is selected from the group consisting of poly(oxyethylene)-poly(oxypropylene) block copolymers and mixtures thereof, and is present in an amount in a range of about 0.01% to about 1.0% (w/v).

15. The method for disinfecting as in claim 13, wherein said buffer is selected from the group consisting of tromethamine, tromethamine salts, phosphate salts, taurine and mixtures thereof in the range of about 0.01% to about 0.5% (w/v).

16. The method for disinfecting as in claim 13, wherein the viscosity-inducing agent is selected from the group consisting of cellulosic derivatives and mixtures thereof in the range of about 0.05% to about 5.0% (w/v) of the total solution.

17. The method for disinfecting as in claim 13, wherein the chelating agent is present in an amount of less than 0.05% (w/v) of the total solution.

18. The method for disinfecting as in claim 13, wherein the tonicity component is present in an amount effective in providing the desired tonicity to said solution.

19. The method for disinfecting as in claim 13, wherein said tonicity component comprises a combination of sodium chloride and potassium chloride and is present in a range of about 0.4% to about 1.5% (w/v).

* * * * *